Figure 1:
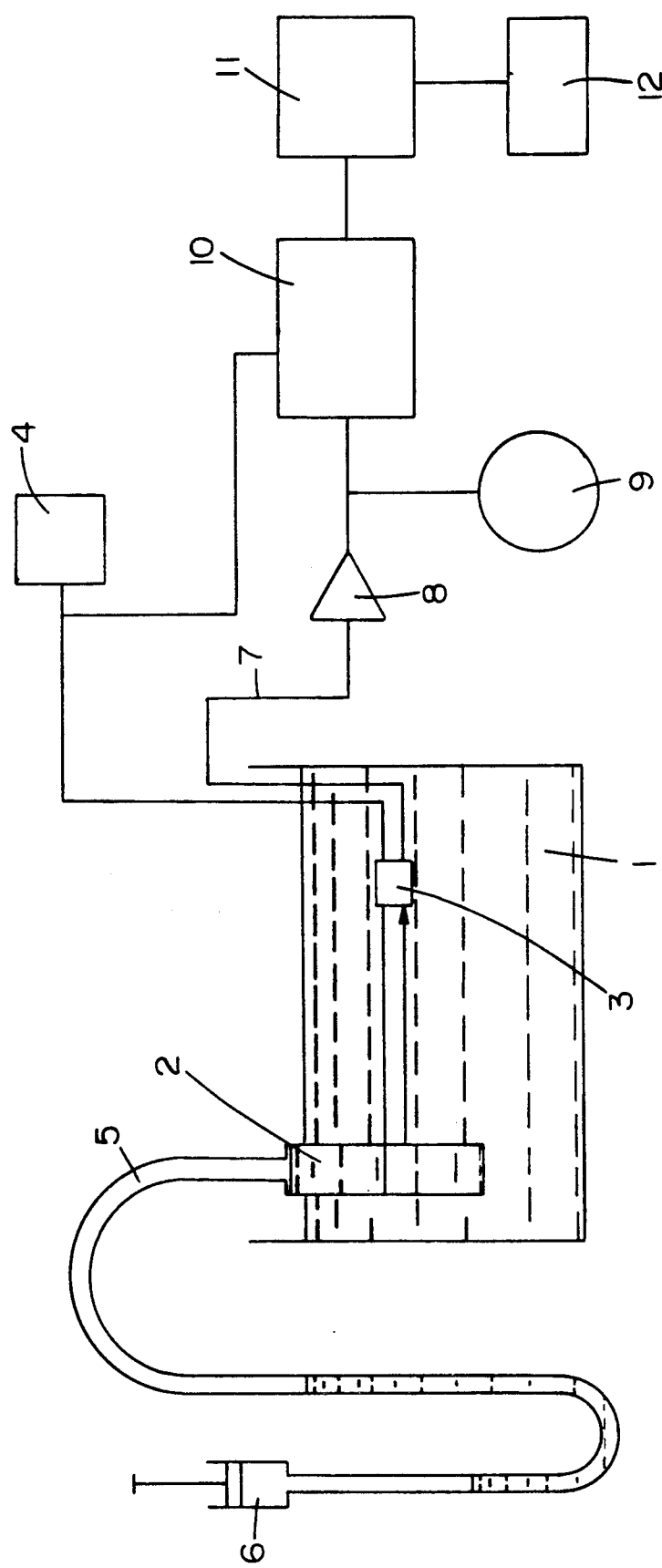

United States Patent [19]

Schlief et al.

[11] Patent Number: 5,195,520
[45] Date of Patent: Mar. 23, 1993

[54] ULTRASONIC MANOMETRY PROCESS IN A FLUID BY MEANS OF MICROBUBBLES

[75] Inventors: Reinhard Schlief; Hans Poland, both of Berlin, Fed. Rep. of Germany

[73] Assignee: Schering Aktiengesellschaft, Berlin and Bergkamen, Fed. Rep. of Germany

[21] Appl. No.: 806,794

[22] Filed: Dec. 12, 1991

[63] Continuation of Ser. No. 350,476, filed as PCT/EP87/00654, Nov. 2, 1987, published as WO88/03388, May 19, 1988, abandoned.

[30] Foreign Application Priority Data

Nov. 5, 1986 [DE] Fed. Rep. of Germany ....... 3637926

[51] Int. Cl.$^5$ ............................................. A61B 8/00
[52] U.S. Cl. ............................ 128/660.02; 128/662.02
[58] Field of Search ....................... 128/660.02, 662.02; 424/9

[56] References Cited

U.S. PATENT DOCUMENTS

| 4,265,251 | 5/1981 | Tickner | 128/660.02 |
| 4,466,442 | 8/1984 | Hilmann et al. | 128/660.02 |
| 4,681,119 | 7/1987 | Rasor et al. | 128/662.02 |

OTHER PUBLICATIONS

Fairbank, W. M. et al., "A New Non-Invasive Technique for Cardiac Pressure Measurement", IEEE BME Trans. vol. BME-24, No. 2 (Mar. 1977) (pp. 107–110).

Primary Examiner—Francis Jaworski
Attorney, Agent, or Firm—Millen, White, Zelano and Branigan

[57] ABSTRACT

The invention relates to an ultrasonic manometry process in a fluid containing stabilized micro bubbles in an ensemble, wherein ultrasonic impulses are radiated into the fluid and brought to interact with the micro bubbles. The amplitude and/or frequency alterations in the ultrasonic scatter signals are recorded and evaluated compared with the ultrasonic impulses radiated in and/or previously recieved. Preparations for measuring blood pressure which can be used with the manometry process are described.

33 Claims, 1 Drawing Sheet

ULTRASONIC MANOMETRY PROCESS IN A FLUID BY MEANS OF MICROBUBBLES

This application is a continuation of application Ser. No. 07/350,476, filed Jul. 5, 1989, based on PCT/EP87/00654 filed Nov. 2, 1987 and now abandoned.

The invention relates to an ultrasonic manometry process according to the preamble of claim 1.

In the journal "IEEE Transaction on Biomedical Engineering, BME-24, no. 2, Mar. 1977" there is a description on pages 107 to 110 of a non-invasive process for measuring the pressure in the heart wherein use is made of the resonance dispersal of the ultrasound through bubbles. Similar sized bubbles of a gas such as for example nitrogen or an inert gas are produced in the fluid whose pressure is to be measured. These bubbles have the same resonance frequency. Broad-band ultrasonic impulses were radiated into the fluid and the spectrum of the ultrasound let through or dispersed was examined. This method of operation originates from a theory based on the interaction of ultrasound and individual bubbles. The resonance frequency displacement in the event of pressure changes was determined. With this process the resonance displacement was calibrated. In this way it was possible to determine the pressure change in a heart chamber.

This measuring technique which is based on the interaction of ultrasound and individual bubbles has not proved satisfactory because the small individual bubbles have too short a service life and larger bubbles are too dangerous, particularly in the case of human beings. Larger bubbles can lead to embolism.

The bubbles used in the process described in the aforementioned literary item are not viable to the lungs owing to their size. These bubbles are no longer present after a venous injection in the arterial region. For this reason after a venous injection with the known process the diastolic and systolic pressures can only be measured in the right vestibule and in the right ventricle, but not in the left vestibule and left ventricle.

In the said citation it was further pointed out that the production of even sized micro bubbles is extremely difficult.

The object of the invention is to provide an ultrasonic manometry process in a fluid whereby clear and reproducible measurements can be made of both pressure changes and pressure absolute values in tube systems, more particularly at any point in the human body, and in particular here at any point in the heart. Starting from a process of the kind mentioned at the beginning this is achieved in accordance with the invention by providing ultrasonic manometry process in a fluid wherein micro bubbles are introduced into the fluid, ultrasonic impulses are radiated into the fluid and are received and evaluated after interaction with the micro bubbles, characterised in that an ensemble, consisting of the micro bubbles and micro particles of a mixture of a semi-solid or fluid boundary surface active substance with a non boundary surface active solid in a fluid carrier, is introduced into the fluid;

ultrasonic manometry process in a fluid wherein micro bubbles are introduced into the fluid, ultrasonic impulses are radiated into the fluid and received and evaluated after interaction with the micro bubbles, characterised in that an ensemble, consisting of the micro bubbles and micro particles of a solid boundary surface active substance in combination with micro particles of a non boundary surface active solid in a fluid carrier is introduced in the fluid; and ultrasonic manometry process in a fluid wherein micro bubbles are introduced into the fluid, ultrasonic impulses are radiated into the fluid and received and evaluated after interaction with the micro bubbles, characterised in that an ensemble, consisting of a fluid mixture for absorbing and stabilising gas bubbles filled with physiologically compatible gas, comprising the mixture of 0.01% to 10% of a tenside or tenside mixture with an aqueous carrier fluid or one miscible with water and the mixture of 0.5% to 50% of a viscosity-increasing substance or a substance mixture in an aqueous carrier fluid or carrier fluid miscible with water, is introduced into the fluid.

Thus in the process according to the invention there are no individual gas bubbles used but rather an ensemble which contains micro bubbles which are stabilised. A cloud-like structure of micro bubbles is produced in the fluid. The stabilised micro bubbles thereby have a service life which is beyond that which can be calculated by physics for a pure fluid. The behaviour of such a micro bubble ensemble is no longer to be described by means of known resonance and scatter models of individual bubbles. Substantially greater reproducible useful signals are produced. A clear reproducible measurement can thereby be carried out which was hitherto not possible in the case of individual bubbles.

It is particularly advantageous to radiate ultrasonic impulses whose frequencies are less than the resonance frequencies of the micro bubbles or equal to same. The fluid pressure conditioned displacement of the resonance absorption towards lower or higher frequencies is then measured in order to measure the pressure changes.

Furthermore it is advantageous to use micro bubbles with a standardized or known and reproducible spectrum of the resonance absorption. The spectral absorption can be determined by means of the ultrasound impulses received in order to establish the absolute value of the momentary fluid pressure. When using micro bubbles with known or standardized resonance spectrum ultrasonic impulses with a predetermined frequency range can be radiated with advantage. Frequency ranges lying outside the frequency range of the radiated ultrasonic impulses can be recorded for evaluation.

To avoid faulty signals ultrasonic impulses can be radiated whose frequencies are in a predetermined ratio to the resonance frequencies of the micro bubbles. Thus in particular n-th harmonic or sub-harmonic frequencies relative to the resonance frequencies can be used. With this process amplitude spectra can be evaluated in the frequency range above the actual frequencies of the micro bubbles. In these ranges the pressure-dependence of the echo amplitudes is mainly independent of the frequency.

It can be advantageous to use micro bubbles with diameters in the range of 0.1 to 500 $\mu$m. Ultrasonic frequencies can thereby be radiated with frequencies in the range from 800 kHz to 5 MHz.

Through the invention a process is provided wherein both the changes in amplitude and the changes in frequency of ultrasonic signals are taken into account which have occurred in interaction with micro bubbles in a fluid.

Furthermore preparations for measuring blood pressure are provided by the invention.

A preferred preparation is formed by dissolving in a fluid solid particles which are free of micro bubbles and contain mainly particles which have a number of gas-filled cavities which are in communication with the surface and a number of cores for a micro bubble formation, more particularly finely dispersed glucose, lactoglucose, maltose or salt with particle sizes in the range from 1 to 5 μm, wherein the ratio of the sizes of the particles to the gas volume of the cavities is selected so that this is sufficient to super-saturate the fluid in which the solid particles are dissolved in the area surrounding the micro bubbles, relative to the gas in the hollow cavities.

An injectable suspension can have an aqueous carrier fluid whose viscosity is substantially greater than that of water. If this preparation is used for measuring blood pressure by means of the ultrasonic manometry process, then the blood vessels can be completely filled with advantage. The micro bubbles produced with the preparation also pass through capillaries of the lungs whereby an intra-arterial pressure measurement is possible after a periphery-venous injection basically at practically any point in the blood vessel system.

A preparation for measuring blood pressure by means of the ultrasonic manometry process can be used which contains micro particles of the mixture of a semi-solid or fluid boundary surface active substance with a non boundary surface active solid in a fluid carrier.

Such preparations according to the invention which can be used as preparations for measuring blood pressure are described in EP OS 123 235.

As an advantage the preparations can contain micro particles which contain as the semi-solid or fluid boundary surface active substance, lecithins, polyoxyethylene fatty acid esters, glycerine polyethylene glycol ricinoleate, polyoxyethylene polyoxypropylene polymers, saccharose esters, xyloglycerides, unsaturated ($C_4$–$C_{20}$) fat alcohols, unsaturated ($C_4$–$C_{20}$) fat acids, mono-, di- and triglycerides, fatty acid esters as micro particles in a volume of 0.01 to 10 percent by weight. Furthermore it is possible that the means contains micro particles which contain as semi-solid or fluid boundary surface active material, butyl stearate, soya oil saccharose glyceride or polyethylene glycol sorbitane monostearate in a concentration of 0.01 to 5 percent by weight, preferably 0.04 to 1 percent by weight. As non boundary surface active solids the preparation can contain cyclodextrines, monosaccharides, disaccharides, trisaccharides, polyols or inorganic or organic salts with a concentration of 5 to 50 percent by weight. The preparation can further contain micro particles which contain as the non boundary surface active solid galactose, lactose or a-cyclodextrine in a concentration of 5 to 50 percent by weight, preferably 9 to 40 percent by weight.

With particular advantage the preparation can contain as physiologically compatible fluid carrier, water, physiological electrolyte solution, the aqueous solution of single or multi-valent alcohols such as glycerine, polyethylene glycol or propylene glycol methyl ester or aqueous solution of a mono or di-saccharides. However water or physiological cooking salt solution can also be contained in the preparation as the physiologically compatible fluid carrier. Furthermore it is proposed that the preparation contains micro particles of a mixture of butyl stearate and glactose in water as well as a mixture of soya oil saccharose glyceride and galactose in water or polyethylene glycol sorbitane monostearate and galactose in physiological cooking salt solution.

Furthermore it was surprisingly found that a preparation according to the invention which contains micro particles of maltose, dextrose, lactose or galactose and gas bubbles in a fluid carrier which is water, a physiological electrolyte solution such as 0.9% aqueous sodium chloride solution, Ringer solution or Tyrode solution or an aqueous solution of maltose, dextrose, lactose or galactose, allows a precise and reliably reproducible blood pressure measurement of organs through which blood flows, such as the heart and veins, without the addition of viscosity-increasing materials such as for example propylene glycol.

Such preparation according to the invention which can be used as preparations for measuring blood pressure are described in EP OS 131 540.

This preparation can thereby contain micro particles of lactose in up to 25% (by weight) aqueous lactose solution. More particularly micro particles of galactose can also be contained in up to 20% aqueous galactose solution or micro particles of galactose in water.

It was surprisingly established that by suspending micro particles of a solid boundary surface active substance if required in combination with micro particles of a non boundary surface active solid in a carrier fluid, micro bubbles are obtained in the form of an ensemble which after injection into a periphery vein allows pressure to be measured in the arterial left ventricle.

Such preparations according to the invention which can be used as preparations for measuring blood pressure are described in EP OS 122 624.

With these preparations, suitable boundary surface active substances for producing the micro particles are all those materials which are physiologically compatible in the amounts used, is which have a low toxocity and/or are biologically decomposable and their melting point is higher than room temperature.

Particularly suitable are lecithins, lecithin fractions and their modification products, polyoxyethylene fatty acid esters such as polyoxyethylene fat alcohol ether, polyoxyethylated sorbitane fatty acid ester, glycerin-polyethylene glycoloxystearate, glycerine polyethylene glycol ricinoleate, ethoxylated soya sterines, ethoxylated ricinus oils and their hydrated derivatives, cholesterol, polyoxyethylene fatty acid stearates and polyoxyethylene polyoxypropylene polymers with molecular weight of 6800–8975, 13300 and 16250, saccharose esters, such as sugar ester, for example saccharose dipalmitate and saccharose monolaurate or saccharose glycerides as well as xyloglycerides, saturated or unsaturated ($C_4$–$C_{20}$) fat alcohols or ($C_4$–$C_{20}$) fatty acids or their metal salts, polyoxyethylene fatty acid esters, mono-, di- and triglycerides, sorbitane fatty acid esters, fatty acid esters of saccharose or fatty acid esters such as butyl stearate and ascorbyl palmitate, wherein calcium stearate, the saccharose ester of lauric acid, stearic acid and palmitic acid as well as ascorbyl palmitate are preferred.

Particularly suitable are boundary surface active substances are those which dissolve relatively poorly in the carrier fluid but relatively easily in the blood. Dissolving the solid material which is rich in enclosed air can be controlled through this jump in the dissolving behaviour.

The boundary surface active substance is used in a concentration of 0.01 to 5 percent by weight, preferably 0.04 to 0.5 percent by weight.

If desired, the micro particles of the boundary surface active substance can be combined with micro particles of a physiologically compatible crystalline solid. Organic or inorganic substances can be used for this, for example salts such as sodium chloride, sodium citrate, sodium acetate or sodium tartrate, monosaccharides, such as glucose, fructose or galactose, disaccharides such as saccharose, lactose or maltose, pentoses such as arabinose, xylose or ribose or cyclodextrins such as α, β or ψ cyclodextrin of which galactose, lactose and α-cyclodextrin are preferred. They are contained in the preparation according to the invention in a concentration of 5 to 50 percent by weight, preferably 9 to 40 percent by weight.

It is furthermore within the scope of the invention for the preparation for measuring blood pressure to be a fluid mixture for absorbing and stabilising gas bubbles filled with physiologically compatible gas, comprising the mixture of 0.01 to 10% of a tenside or tenside mixture with an aqueous or water-miscible carrier fluid and the mixture of 0.5% to 50% of a viscosity-increasing substance or a substance mixture in an aqueous or water-miscible carrier fluid wherein both mixtures exist separately or combined.

Such preparations according to the invention which can be used for measuring blood pressure are described in EP PS 0 077 752.

Both non-ionogenic and ionogenic tensides are suitable as tensides. Non-ionogenic tensides can be: lecithins, lecithin fractions and their modification products, polyoxyethylene fatty acid esters such as polyoxyethylene fat alcohol ether, polyoxyethylated sorbitane fatty acid esters, glycerine polyethylene glycoloxy stearate, glycerine polyethylene glycol ricinoleate, ethyl oxy soya sterines, ethyloxy ricinus oils and their hdyrated derivatives, cholesterol, polyoxyethylene polyoxypropylene polymers wherein polyoxyethylene fatty acid stearates and polyoxyethylene polyoxypropylene polymers with the molecular weight 6800–8975, 13300 and 16250 are preferred. All percentages relate to percents by weight.

Ionogenic tensides can be: Quarternay ammonium bases, sodium lauryl sulfate, sodium dioctyl sulfosuccinate.

The preparation solution can thereby contain 0.01 to 10% of a tenside or the mixture of several tensides wherein the preferred content is 0.5 to 5% tenside or tenside mixture.

The viscosity-increasing substances may be mono or polysaccharides such as glucose, levulose, galactose, lactose, sorbite, mannite, xylite, saccharose or dextrane, cyclodextrins, hydroxyethyl starch and polyols. The polyols used can be glycerine, polyglycol, inulin and 1,2-propane diol. The following can be used to increase the viscosity: proteins, protein-like substances, amino acids or blood substitutes such as for example plasma proteins, gelatines, oxypolygalatines and galatine derivatives or mixtures thereof.

The concentration of these said substances in the solution can amount to 0.5 to 50% wherein the maximum concentration also depends on the substance dissolved. Thus for example glucose or lactose can be used with a concentration of 0.5 to 50% whilst gelatine has a preferred concentration of 0.5 to 2%. The oxypolygelatine is preferably used with a concentration of 0.5 to 10%.

Tensides can also be used which act at the same time to increase the viscosity, such as for example polyoxyethylene polyoxypropylene polymers with the molecular weight of 4750 to 16250.

In this case the concentration of the tensides with viscosity-increasing effect mounts to 1% to 20%, preferably 3 to 10%. The tenside or tenside mixture is preferably dissolved in a carrier fluid in the presence of the viscosity increasing substance or substance mixture. The carrier fluid can be water or aqueous solutions which are physiologically compatible such as for example physiological electrolyte solutions such as physiological cooking salt solution, Ringer solution or the aqueous solutions of sodium chloride, calcium chloride, sodium hydrogen carbonate, sodium citrate, sodium acetate or sodium tartrate or salt solutions, such as are normally used as infusion solutions.

Embodiments of the invention will now be explained in the following description with reference to the drawing in which:

FIG. 1 is a diagrammatic illustration of a test unit for carrying out the process.

As shown in FIG. 1, a rectangular double-chamber plexiglass bulb 2 with plano-parallel front and back walls as well as a sound head 3 with transmitter and receiver function are mounted in a water bath 1. The sound head 3 is connected to an impulse transmitter 4. Different sound heads 3 with suitable wide band impulse characteristics were used for the different frequency ranges 800 KHz to 2.2 MHz and 2.2 MHz to 4.2 MHz. As illustrated beaming was conducted at 90° to the front wall.

The plexiglass bulb 2 is connected by a pipeline 5 to the pressure transmitter 6.

The output of the sound head 3 is connected by the lead 7 to an amplifier 8 whose output as shown is connected to an oscillograph 9 and a comparator circuit 10. A further input of the comparator circuit 10 is as illustrated connected to the impulse transmitter 4. The output of the comparator circuit is connected to a laboratory computer 11 whose output feeds a printer 12.

The back wall echo, or in the case of a highly concentrated suspension the signal scattered back by the ensemble with micro bubbles is amplified and shown up on the oscillograph and then examined by means of a frequency analyzer. After A/D conversion the measured data were stored in a laboratory computer 11 so that the possibility of an additional evaluation is available. For example digital filtering or a graphic illustration could be undertaken.

We claim:

1. An ultrasonic manometry process in a fluid comprising introducing microbubbles into a fluid, radiating ultrasonic impulses into the fluid, and receiving and evaluating ultrasonic impulses after interaction of the radiated ultrasonic impulses with the microbubbles to determine fluid pressure, wherein the frequency range of ultrasonic impulses which are received and evaluated lie outside of the frequency range of the ultrasonic impulses radiated into the fluid and wherein the microbubbles are those created by introducing into the fluid an ensemble comprising the microbubbles and microparticles of a mixture of a semi-solid or fluid boundary surface active substance with a non-boundary surface active solid in a fluid carrier.

2. A process according to claim 1, wherein an ensemble with a known or standardized resonance spectrum is introduced into the fluid, ultrasonic impulses with a predetermined frequency range are radiated and frequencies are registered and evaluated which lie outside of the frequency range of the radiated ultrasonic impulses.

3. A process according to claim 2, wherein ultrasonic impulses are radiated whose frequencies are in an n-th harmonic or sub-harmonic ratio to the resonance frequencies of the ensemble.

4. A process according to claim 1, wherein signal spectra in the frequency range above the resonance frequency of the ensemble are registered and evaluated.

5. A process according to claim 1, wherein microbubbles with diameters in the range of 0.1 to 500 μm are used.

6. A process according to claim 1, wherein ultrasonic frequencies in the range from 800 kHz to 5 MHz are radiated in.

7. A process according to claim 1, wherein the ensemble contains as the semi-solid or fluid boundary surface active substance lecithins, polyoxyethylene fatty acid esters, glycerine polyethylene glycol ricinoleate, polyoxyethylene polyoxypropylene polymers, saccharose esters, xyloglycerides, unsaturated ($C_4$–$C_{20}$) fatty alcohols, unsaturated ($C_4$–$C_{20}$) fatty acids, mono-, di-, or triglycerides, or fatty acid esters as microparticles in a volume of 0.01 to 10 percent by weight.

8. A process according to claim 7, wherein the ensemble contains as the semi-solid or fluid boundary surface active substance butyl stearate, soya oil saccharose glyceride or polyethylene glycol sorbitane monostearate in a concention of 0.01 to 5 percent by weight.

9. A process according to claim 7, wherein the ensemble contains as the non-boundary surface active solid cyclodextrins, monosaccharides, disaccharides, trisaccharides, polyols or inorganic or organic salts with a concention of 5 to 50 percent by weight.

10. A process according to claim 7, wherein the ensemble contains as the non-boundary surface active solid galactose, lactose, or α-cyclodextrin in a concentration of 5 to 50 percent by weight.

11. A process according to 7, wherein the ensemble contains as the fluid carrier which is physiologically compatible water, physiological electrolyte solution, an aqueous solution of single or multi-valent alcohols or the aqueous solution of a mono- or disaccharide.

12. A process according to claim 7, wherein the ensemble contains microparticles of a mixture of butyl stearate and galactose in water.

13. A process according to claim 7, wherein the ensemble contains microparticles of a mixture of soya oil saccharose glyceride and galactose in water.

14. A process according to claim 7, wherein the ensemble contains microparticles of a mixture of polyethylene glycol sorbitane monostearate and galactose in a physiological cooking salt solution.

15. A process according to claim 7, wherein the ensemble contains microparticles of maltose, dextrose, lactose, or galactose and gas bubbles in a fluid carrier wherein the fluid carrier consists of water, physiological electrolyte solution, or an aqueous solution of maltose, dextrose, lactose, or galactose.

16. A process according to claim 15, wherein the ensemble contains microparticles of lactose in up to 25% (percent by weight) aqueous lactose solution.

17. A process according to claim 15, wherein the ensemble contains microparticles of galactose in up to 20% aqueous galactose solution.

18. An ultrasonic manometry process in a fluid comprising introducing microbubbles into a fluid, radiating ultrasonic impulses into the fluid, and receiving and evaluating ultrasonic impulses after interaction of the radiated ultrasonic impulses with the microbubbles to determine fluid pressure, wherein the frequency range of ultrasonic impulses which are received and evaluated lie outside of the frequency range of the ultrasonic impulses radiated into the fluid and wherein the microbubbles are those created by introducing into the fluid an ensemble comprising the microbubbles and microparticles of a solid boundary surface active substance in combination with microparticles of a non-boundary surface active solid in a fluid carrier.

19. A process according to claim 18, wherein the ensemble contains as the solid boundary active substance lecithins, polyoxyethylene fatty acid esters, glycerine polyethylene glycol ricinoleate, cholesterol, polyoxyethylene polyoxypropylene polymers, saccharose esters, xyloglycerides, saturated or unsaturated ($C_4$–$C_{20}$) fatty alcohols, saturated or unsaturated ($C_4$–$C_{20}$) fatty acids or their metal salts, mono, di-, or triglycerides, or fatty acid esters as microparticles in a volume of 0.01 to 10 percent by weight.

20. A process according to claim 18, wherein the ensemble contains magnesium stearate, ascorbyl palmitate, saccharose monopalmitate, saccharose monostearate, or saccharose distearate as solid boundary surface active substance in the form of microparticles in a concentration of 0.01 to 5 percent by weight.

21. A process according to claim 18, wherein the ensemble contains as the microparticles of a non-boundary surface active solid cyclodextrins, monosaccharides, disaccharides, trisaccharides, polyols, or inorganic or organic salts as the microparticles with a concentration of 5 to 50 percent by weight.

22. A process according to claim 18, wherein the ensemble contains as the non-boundary surface active solid galactose, lactose, or α-cyclodextrin as microparticles in a concentration of 5 to 50 percent by weight.

23. A process according to claim 18, wherein the ensemble contains as the fluid carrier which is physiologically compatible water, physiological electrolyte solution, an aqueous solution of single or multi-valent alcohols, or an aqueous solution of a mono- or disaccharide.

24. A process according to claim 18, wherein the ensemble contains as the physiologically compatible fluid carrier water, physiologically cooking salt solution, 10% aqueous lactose solution, or 20% aqueous galactose solution.

25. A process according to claim 18, wherein the ensemble contains microparticles of magnesium stearate and galactose, in a 20% aqueous galactose solution.

26. An ultrasonic manometry process in a fluid comprising introducing microbubbles into a fluid, radiating ultrasonic impulses into the fluid, and receiving and evaluating ultrasonic impulses after interaction of the radiated ultrasonic impulses with the microbubbles to determine fluid pressure, wherein the frequency range of ultrasonic impulses which are received and evaluated lie outside of the frequency range of the ultrasonic impulses radiated into the fluid and wherein the microbubbles are those created by introducing into the fluid an ensemble comprising a fluid mixture for absorbing and stabilizing gas bubbles filled with physiologically compatible gas, comprising the mixture of 0.01% to 10% of a tenside or tenside mixture with an aqueous carrier fluid or one miscible with water and the mixture of 0.5% to 50% of a viscosity-increasing substance or a substance mixture in an aqueous carrier fluid or carrier fluid miscible with water.

27. Preparation for measuring blood pressure by means of the ultrasonic manometry process according to claim 26 comprising
a fluid mixture for absorbing and stabilising gas bubbles filled with physiologically compatible gas, consisting of the mixture of 0.01% to 10% of a tenside or tenside mixture with an aqueous carrier fluid or carrier fluid miscible with water and the mixture of 0.5% to 50% of a viscosity-increasing substance or a substance mixture in an aqueous or water-miscible carrier fluid, wherein the two mixtures exist separately or combined.

28. A process according to claim 26, wherein the ensemble contains the mixture of 0.01 to 10% of a tenside or tenside mixture in an aqueous or water-miscible carrier fluid which contains 0.05 to 5% of a physiologically compatible carbonic acid salt and the mixture of 0.5% to 50% of a viscosity increasing substance or a substance mixture with an aqueous or water-miscible carrier fluid which contains an amount of physiologically compatible acid equivalent to the carbonic acid salt.

29. A process according to claim 26, wherein the ensemble contains a non-iongenic tenside.

30. A process according to claim 29, wherein the ensemble contains as a non-iongenic tenside polyoxyethylene polyoxypropylene polymers with the molecular weight 6800 to 8975 or 16250 to 13300.

31. A process according to claim 29, wherein the ensemble contains as a non-iongenic tenside a polyoxyethylene fatty acid ester or polyoxyethylene stearate.

32. A process according to claim 26, wherein the ensemble contains an iongenic tenside which is sodium lauryl sulfate or sodium dioctylsulfosuccinate.

33. A process according to claim 26, wherein the ensemble contains as the carrier fluid water or water-miscible, single or multi-valent alcohols, physiological electrolyte solution, or an infusion solution or mixtures thereof.

* * * * *